United States Patent
Lakatos et al.

(10) Patent No.: US 8,733,670 B2
(45) Date of Patent: May 27, 2014

(54) CONTAINER FOR HOLDING A VOLATILE MATERIAL AND A WICK

(75) Inventors: Kara L. Lakatos, Racine, WI (US); Ralph Schwarz, Racine, WI (US); Tyler D. Duston, Evanston, ID (US)

(73) Assignee: S.C. Johnson & Son, Inc., Racine, WI (US)

( * ) Notice: Subject to any disclaimer, the term of this patent is extended or adjusted under 35 U.S.C. 154(b) by 230 days.

(21) Appl. No.: 12/711,684

(22) Filed: Feb. 24, 2010

(65) Prior Publication Data

US 2010/0147972 A1    Jun. 17, 2010

Related U.S. Application Data (60) Division of application No. 11/341,166, filed on Jan. 27, 2006, now abandoned, which is a continuation-in-part of application No. 10/266,798, filed on Oct. 8, 2002, now abandoned, and a continuation-in-part of application No. 10/266,512, filed on Oct. 8, 2002, now Pat. No. 7,007,863, and a continuation-in-part of application No. 10/394,621, filed on Mar. 21, 2003, now Pat. No. 7,032,831, and a continuation-in-part of application No. 10/394,623, filed on Mar. 21, 2003, now Pat. No. 7,244,398, and a continuation-in-part of application No. 10/607,702, filed on Jun. 27, 2003, now abandoned, and a continuation-in-part of application No. 10/609,843, filed on Jun. 30, 2003, now Pat. No. 7,309,024.

(51) Int. Cl.
*A61L 9/04* (2006.01)

(52) U.S. Cl.
USPC ............... 239/44; 239/145; 239/326

(58) Field of Classification Search
USPC .............................. 239/51.5, 145, 326, 34–60
See application file for complete search history.

(56) References Cited

U.S. PATENT DOCUMENTS

| 929,254 | A | * | 7/1909 | Sholes | ........................... 239/45 |
|---|---|---|---|---|---|
| 1,058,808 | A | | 4/1913 | Thilges | |
| 1,129,897 | A | | 3/1915 | Owen, Jr. | |
| 1,911,871 | A | | 5/1933 | Anderson | |
| 2,336,675 | A | * | 12/1943 | Damon | ......................... 264/136 |

(Continued)

FOREIGN PATENT DOCUMENTS

| AU | 664685 | 11/1995 |
|---|---|---|
| DE | 29 907 125 U1 | 7/1999 |

(Continued)

OTHER PUBLICATIONS

International Search Report and Written Opinion, Aug. 16, 2004, Appl. No. PCT-US04-008436.

(Continued)

*Primary Examiner* — Jason Boeckmann (57) ABSTRACT

A wick assembly for use in a dispenser for a volatile liquid includes a wick having an external surface and a discontinuity in the surface providing a location in the wick of less resistance to a force applied to the wick than a location adjacent to the discontinuity. In one embodiment, the wick is adapted to be positioned to extend from an inside of a container, through an opening defined in the container, to an outside of the container, and the wick is formed such that a portion of the wick will block the opening when the wick is broken at the discontinuity.

18 Claims, 3 Drawing Sheets

(56) References Cited

U.S. PATENT DOCUMENTS

| | | | |
|---|---|---|---|
| 2,435,811 A | 2/1948 | Waters | |
| 2,557,501 A | 6/1951 | Fusay et al. | |
| 2,668,993 A | 2/1954 | Bair | |
| 2,741,812 A | 4/1956 | Tellier | |
| 2,754,554 A | 7/1956 | Mills | |
| 2,764,789 A | 10/1956 | Zelenka | |
| 2,828,953 A | 4/1958 | Hartmann | |
| 2,867,866 A | 1/1959 | Steele | |
| 2,899,532 A | 8/1959 | Reick | |
| 2,931,880 A | 4/1960 | Yaffe | |
| 3,080,624 A | 3/1963 | Weber, III | |
| 3,522,935 A | 8/1970 | Lewis | |
| 3,550,853 A | 12/1970 | Gray | |
| 3,587,968 A | 6/1971 | Balland et al. | |
| 3,633,881 A | 1/1972 | Yurdin et al. | |
| 3,748,464 A | 7/1973 | Andeweg | |
| 3,749,904 A | 7/1973 | Graff | |
| 3,761,702 A | 9/1973 | Andeweg | |
| 3,790,081 A | 2/1974 | Thornton | |
| 3,890,085 A | 6/1975 | Andeweg | |
| 3,923,458 A | 12/1975 | Moran | |
| 3,948,445 A | 4/1976 | Andeweg | |
| 3,990,848 A | 11/1976 | Corris | |
| 3,993,444 A | 11/1976 | Brown | |
| 4,035,451 A | 7/1977 | Tringali | |
| 4,059,422 A | 11/1977 | Steiner | |
| 4,166,087 A | 8/1979 | Cline | |
| 4,173,604 A | 11/1979 | Dimacopoulos | |
| 4,219,964 A * | 9/1980 | Dale | 47/1.5 |
| 4,276,236 A | 6/1981 | Sullivan | |
| 4,294,778 A | 10/1981 | DeLuca | |
| 4,301,095 A | 11/1981 | Mettler et al. | |
| 4,323,193 A | 4/1982 | Compton | |
| 4,346,059 A | 8/1982 | Spector | |
| 4,370,300 A | 1/1983 | Mori et al. | |
| 4,383,951 A | 5/1983 | Palson | |
| 4,387,849 A | 6/1983 | Van Loveren et al. | |
| 4,419,326 A | 12/1983 | Santini | |
| 4,432,938 A | 2/1984 | Meetze, Jr. | |
| 4,477,414 A | 10/1984 | Muramoto et al. | |
| 4,493,011 A | 1/1985 | Spector | |
| 4,605,165 A | 8/1986 | Van Loveren et al. | |
| 4,614,211 A | 9/1986 | Mettler | |
| 4,621,768 A | 11/1986 | Lhoste et al. | |
| 4,660,764 A | 4/1987 | Joyaux et al. | |
| 4,666,638 A | 5/1987 | Baker | |
| 4,695,435 A | 9/1987 | Spector | |
| 4,707,338 A | 11/1987 | Spector | |
| 4,739,928 A | 4/1988 | O'Neil | |
| 4,743,406 A | 5/1988 | Steiner et al. | |
| 4,768,676 A | 9/1988 | Kaneko | |
| 4,774,032 A | 9/1988 | Coates et al. | |
| 4,857,240 A | 8/1989 | Kearnes et al. | |
| 4,866,580 A | 9/1989 | Blackerby | |
| 4,913,350 A | 4/1990 | Purzycki | |
| 4,928,881 A | 5/1990 | Barlics et al. | |
| 4,931,224 A | 6/1990 | Holzner, Sr. | |
| 4,968,487 A | 11/1990 | Yamamoto et al. | |
| 5,000,383 A | 3/1991 | van der Heijden | |
| 5,014,913 A | 5/1991 | Hoyt et al. | |
| RE33,864 E | 3/1992 | Steiner | |
| 5,094,025 A | 3/1992 | Daniels | |
| 5,095,647 A | 3/1992 | Zobele et al. | |
| 5,114,625 A | 5/1992 | Gibson | |
| 5,126,078 A | 6/1992 | Steiner et al. | |
| 5,133,042 A | 7/1992 | Pelonis | |
| 5,217,696 A | 6/1993 | Wolverton et al. | |
| 5,222,186 A | 6/1993 | Schimanski et al. | |
| 5,223,182 A | 6/1993 | Steiner et al. | |
| 5,334,162 A | 8/1994 | Harris | |
| 5,342,584 A | 8/1994 | Fritz et al. | |
| 5,370,829 A | 12/1994 | Kunze | |
| 5,376,338 A | 12/1994 | Zlotnik | |
| 5,402,517 A | 3/1995 | Gillett et al. | |
| 5,431,885 A | 7/1995 | Zlotnik et al. | |
| 5,437,410 A | 8/1995 | Babasade | |
| 5,534,229 A | 7/1996 | Nomura et al. | |
| 5,547,616 A | 8/1996 | Dancs et al. | |
| 5,647,053 A | 7/1997 | Schroeder et al. | |
| 5,651,942 A | 7/1997 | Christensen | |
| 5,662,835 A | 9/1997 | Collingwood | |
| D386,974 S | 12/1997 | Wefler | |
| D393,063 S | 3/1998 | Wefler | |
| 5,725,152 A | 3/1998 | Akyu | |
| 5,800,741 A | 9/1998 | Glenn et al. | |
| 5,802,865 A | 9/1998 | Strauss | |
| 5,840,246 A | 11/1998 | Hammons et al. | |
| 5,857,620 A | 1/1999 | Nakoneczny | |
| 5,876,678 A | 3/1999 | Harrell et al. | |
| 5,891,400 A | 4/1999 | Ansari et al. | |
| 5,909,845 A * | 6/1999 | Greatbatch et al. | 239/44 |
| 5,919,423 A | 7/1999 | Requejo et al. | |
| 5,932,147 A | 8/1999 | Chen | |
| 5,945,094 A | 8/1999 | Martin et al. | |
| 5,970,643 A | 10/1999 | Gawel, Jr. | |
| 5,980,064 A | 11/1999 | Metroyanis | |
| 6,017,139 A | 1/2000 | Lederer | |
| 6,044,202 A | 3/2000 | Junkel | |
| 6,104,867 A | 8/2000 | Stathakis et al. | |
| 6,105,916 A | 8/2000 | Zlotnik et al. | |
| 6,106,786 A | 8/2000 | Akahoshi | |
| 6,145,241 A | 11/2000 | Okuno | |
| 6,189,327 B1 | 2/2001 | Strauss et al. | |
| 6,196,706 B1 | 3/2001 | Cutts | |
| 6,236,807 B1 | 5/2001 | Ruffolo et al. | |
| 6,241,161 B1 | 6/2001 | Corbett | |
| 6,254,065 B1 | 7/2001 | Ehrensperger et al. | |
| 6,354,710 B1 | 3/2002 | Nacouzi | |
| 6,361,752 B1 | 3/2002 | Demarest et al. | |
| 6,371,450 B1 | 4/2002 | Davis et al. | |
| 6,391,329 B1 | 5/2002 | Ito et al. | |
| 6,416,242 B1 | 7/2002 | Kaufmann | |
| 6,454,425 B1 | 9/2002 | Lin | |
| 6,484,438 B2 | 11/2002 | Matsunaga et al. | |
| 6,514,467 B1 * | 2/2003 | Bulsink et al. | 422/122 |
| 6,555,068 B2 | 4/2003 | Smith | |
| 6,567,613 B2 | 5/2003 | Rymer | |
| 6,616,308 B2 | 9/2003 | Jensen et al. | |
| 6,619,560 B1 | 9/2003 | Chun | |
| 6,697,571 B2 | 2/2004 | Triplett et al. | |
| 6,699,432 B2 | 3/2004 | Channer | |
| 6,766,817 B2 | 7/2004 | da Silva | |
| 6,775,470 B2 | 8/2004 | Zobele et al. | |
| 6,793,149 B2 | 9/2004 | Schramm | |
| 6,862,403 B2 | 3/2005 | Pedrotti et al. | |
| 6,871,794 B2 | 3/2005 | McEwen | |
| 6,899,280 B2 | 5/2005 | Kotary et al. | |
| 6,909,840 B2 | 6/2005 | Harwig et al. | |
| 6,917,754 B2 | 7/2005 | Pedrotti et al. | |
| 6,921,025 B2 | 7/2005 | Hart et al. | |
| 6,938,883 B2 | 9/2005 | Adams et al. | |
| 6,966,665 B2 | 11/2005 | Limburg et al. | |
| 6,996,335 B2 | 2/2006 | Zobele | |
| 7,007,863 B2 | 3/2006 | Kotary et al. | |
| 7,014,818 B2 | 3/2006 | Rymer | |
| 7,018,644 B2 | 3/2006 | Lang | |
| 7,032,831 B2 | 4/2006 | Duston et al. | |
| 7,168,631 B2 | 1/2007 | Jones | |
| 7,997,508 B2 | 8/2011 | Motylinski et al. | |
| 2002/0080601 A1 | 6/2002 | Meltzer | |
| 2002/0093834 A1 | 7/2002 | Yu et al. | |
| 2002/0136542 A1 * | 9/2002 | He et al. | 392/395 |
| 2002/0136886 A1 | 9/2002 | He et al. | |
| 2003/0005620 A1 | 1/2003 | Ananth et al. | |
| 2003/0007887 A1 | 1/2003 | Roumpos et al. | |
| 2003/0053305 A1 | 3/2003 | Lin | |
| 2004/0060997 A1 * | 4/2004 | Jones | 239/44 |
| 2004/0074982 A1 | 4/2004 | Kotary et al. | |
| 2004/0141315 A1 | 7/2004 | Sherburne | |
| 2004/0184969 A1 | 9/2004 | Kotary et al. | |
| 2004/0246711 A1 | 12/2004 | Brenchley et al. | |
| 2004/0257798 A1 | 12/2004 | Hart | |
| 2004/0262419 A1 | 12/2004 | Kotary et al. | |
| 2004/0262420 A1 | 12/2004 | Hansen et al. | |

(56) References Cited

U.S. PATENT DOCUMENTS

| | | |
|---|---|---|
| 2004/0265189 A1 | 12/2004 | Schwarz |
| 2004/0265196 A1 | 12/2004 | Varanasi et al. |
| 2005/0053368 A1 | 3/2005 | Pesu et al. |
| 2005/0178345 A1 | 8/2005 | Crapser |
| 2005/0185392 A1 | 8/2005 | Walter et al. |
| 2006/0163376 A1 | 7/2006 | Lakatos et al. |

FOREIGN PATENT DOCUMENTS

| | | |
|---|---|---|
| DM | 054926 | 9/2000 |
| EP | 0 882 459 | 12/1998 |
| EP | 1 031 446 | 8/2000 |
| EP | 1 270 021 | 1/2003 |
| EP | 1 283 062 | 2/2003 |
| EP | 1 392 368 | 10/2003 |
| GB | 2 285 579 | 7/1995 |
| WO | WO 95/10352 | 4/1995 |
| WO | WO 97/13539 | 4/1997 |
| WO | WO 98/19526 | 5/1998 |
| WO | WO 01/02025 | 1/2001 |
| WO | WO 01/23008 | 4/2001 |
| WO | WO 02/30220 | 4/2002 |
| WO | WO 02/31413 | 4/2002 |
| WO | WO 03/013618 | 2/2003 |
| WO | WO 03/028775 | 4/2003 |
| WO | WO 03/086487 | 10/2003 |
| WO | WO 03/092750 | 11/2003 |
| WO | WO 2004/030708 | 4/2004 |

OTHER PUBLICATIONS

International Search Report and Written Opinion, Aug. 16, 2004, Appl. No. PCT-US04-008437.
International Search Report and Written Opinion dated Nov. 30, 2004, Appl. No. PCT-US2004-020586.
"Inglow™Candle Company" www.inglowcandle.com (2002).
"Luna Candles" http://www.epartyunlimited.com-luna-candles.html (print date 2004).
Office Action in U.S. Appl. No. 10/608,357 dated Sep. 5, 2008.
Office Action in U.S. Appl. No. 11/341,166 dated Jun. 5, 2008.
Office Action in U.S. Appl. No. 11/341,166 dated Aug. 29, 2008.
Office Action in U.S. Appl. No. 11/341,166 dated Dec. 31, 2008.
Office Action in U.S. Appl. No. 11/341,166 dated Apr. 24, 2009.
Office Action in U.S. Appl. No. 11/341,166 dated Nov. 4, 2009.
Office Action in U.S. Appl. No. 11/341,166 dated Jan. 15, 2010.

* cited by examiner

CONTAINER FOR HOLDING A VOLATILE MATERIAL AND A WICK

CROSS REFERENCE TO RELATED APPLICATIONS

This application is a divisional of U.S. patent application Ser. No. 11/341,166, filed Jan. 27, 2006, which is a continuation-in-part of each of U.S. patent application Ser. No. 10/266,798, filed Oct. 8, 2002, Ser. No. 10/266,512, filed Oct. 8, 2002, Ser. No. 10/394,621, filed Mar. 21, 2003, Ser. No. 10/394,623, filed Mar. 21, 2003, Ser. No. 10/607,702, filed Jun. 27, 2003, and Ser. No. 10/609,843, filed Jun. 30, 2003, each of which is incorporated by reference herein in the entirety thereof.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to wicks for dispensing a volatile liquid and, more particularly, wicks which project from a container holding the volatile liquid.

2. Description of the Background of the Invention

Apparatus is known for dispensing volatile actives into the surrounding environment. Many such apparatuses include a container for containing a liquid that carries the volatile active and a soft, pliable wick extending through an opening in the container. The wick is in contact with the liquid inside the container so that the liquid can migrate by capillary action up the wick to an exterior side of the opening, where the volatile active is able to disperse into the surrounding environment.

SUMMARY OF THE INVENTION

In one aspect of the invention, a wick assembly for use in a dispenser for a volatile liquid includes a wick having an external surface and a discontinuity formed in the surface providing a location in the wick of less resistance to a force applied to the wick than a location adjacent to the discontinuity. The discontinuity is disposed between a portion of the wick adapted to reside substantially inside the dispenser and a portion of the wick adapted to reside substantially outside the dispenser.

In another aspect of the invention, A wick assembly for use in a dispenser for a volatile liquid includes a wick having an external surface, a discontinuity formed in the surface providing a location in the wick of less resistance to a force applied to the wick than a location adjacent to the discontinuity, and a retention member defining an opening adapted to be received in another opening of a container for holding the volatile liquid. The opening of the retention member receives a portion of the wick therein. The portion of the wick received in the opening of the retention member forms an interference fit with the retention member.

In a further aspect of the invention, a wick assembly for use in a dispenser for volatile liquid includes a wick adapted to be positioned to extend from an inside of a container for holding the volatile liquid, through an opening defined in the container, and to an outside of the container. The wick assembly further includes means for enabling the wick to separate into at least two portions wherein one of the portions blocks the opening of the container.

Other aspects and advantages of the present invention will become apparent upon consideration of the following detailed description.

BRIEF DESCRIPTION OF THE DRAWINGS

FIG. 19 is a side elevational view of a ninth embodiment of the wick of the present invention;

DETAILED DESCRIPTION

Figure 1:
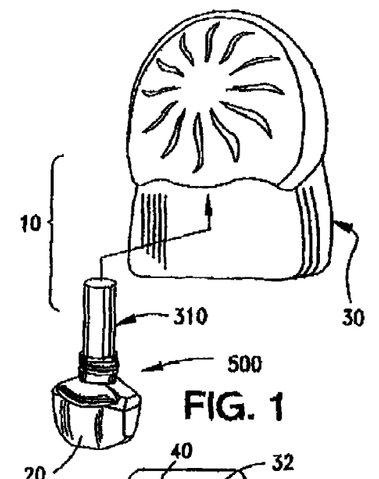
FIG. 1 is a perspective view showing insertion of the wick of the present invention into a housing of a dispensing device.
Figure 2:
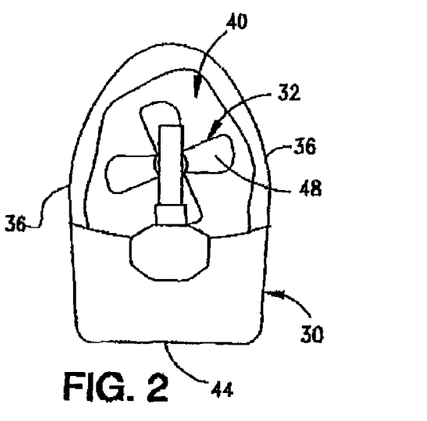
FIG. 2 is a front schematic view of the dispenser assembled of FIG. 1 showing the dispenser housing partially cut away.
Figure 2A:
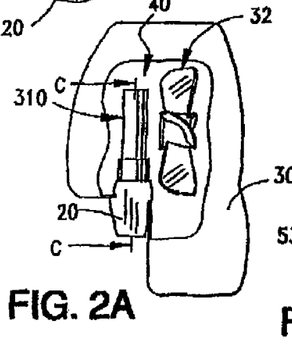
FIG. 2A is a side elevational view showing the dispenser assembled of FIG. 1 with the housing partially cut away.

Referring to FIGS. 1, 2 and 2A, a wick assembly, generally designated 500, is designed for use in a volatile liquid dispenser 10. Liquid dispenser 10 is designed to disseminate a volatile liquid, such as a fragrance compound, into a room. The fragrance compound is disseminated via a forced air stream flowing around a wick, generally designated 310, at room ambient temperature. According to the present invention, dispenser 10 includes a housing 30, a motorized fan 32 mounted in housing 30 for generating the air stream, and a wick 310 coupled to housing 30, wherein wick 310 may be formed from a plastic material such as nylon ultra high molecular weight high density polyethylene, or high density polypropylene.

In referring to FIG. 2, housing 30 includes sidewalls 36 and back wall (not shown) to form an interior 40. Base 44 is configured to be able to place dispenser 10 on a flat surface and is a convenient location to position the battery for motorized fan 32. The air stream to impact and pass around wick 310 is generated by the rotation of blades 48.

Portions of housing 30 form an enclosure 40 for fan 32 and for receiving wick 310 of wick assembly 500 into the air stream generated by fan 32. Wick 310 is to be positioned and secured in enclosure 40 formed by housing 30 so as to reside in the air stream generated by fan 32. Wick 310 may be secured in the desired position by coupling wick assembly 500 to dispenser housing 30 using any one of numerous methods. As generally shown in FIG. 2A, container 20 can carry detents or grooves in its sidewalls which will engage housing 30 and thereby releasably secure container 20 to housing 30. Other ways of securing container 20 to housing 30 may include contact adhesives and/or hook and loop fasteners, for example.

The volatile liquid migrates along wick 310 from the volatile liquid in reservoir 20 to a portion of wick 310 immersed in an air stream generated by fan 32, where it is evaporated from the surface of wick 310 by forced airflow generated by fan 32.

FIGS. 3-20 show various embodiments of wicks and wick assemblies of the present invention. In cross-sectional views showing the wicks alone, the cross section is generally taken along a length of the wick. In showing embodiments of wick assembly 500, the cross-sections will be taken along line C-C shown in FIG. 2A.

Figures 3, 4:
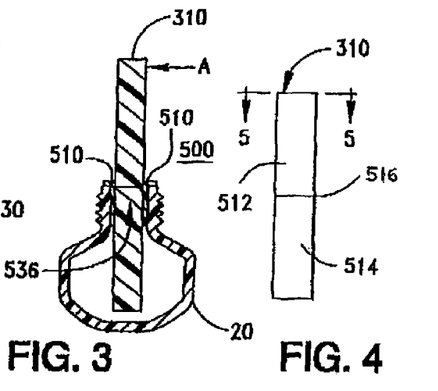
FIG. 3 is a cross-sectional view taken along line c-c of FIG. 2A of the present invention.
FIG. 4 is a side elevational view of the wick of the present invention.

In one example, FIG. 3 shows an embodiment of the wick assembly 500 of the present invention which includes wick 310 secured in a container 20 acting as a reservoir for the volatile liquid. Container 20 defines an opening 536 in which wick 310 may be received and secured. When wick assembly 500 includes a container 20, one portion of wick 310 will reside inside container 20 in contact with the volatile liquid held by the container, while another portion of wick 310 resides outside the container. To prevent leakage of volatile liquid from container 20, a seal is formed between wick 310 and container 20 along the portion of wick 20 which transitions from the inside of container 20 to the outside of the container.

Figure 21:
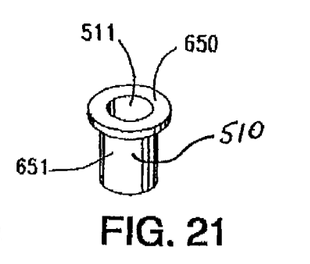
FIG. 21 is a perspective view of a retention member of the present invention.

Referring to FIGS. 3 and 21, wick 310 may be secured in a retention member 510 (FIG. 21). Retention member 510 has a generally annular shaped body 651 defining an opening 511 for receiving wick 310 therein, a pair of opposite ends and a flange 650 at one end which abuts an end of container opening 536 (as shown in FIG. 3) when retention member 510 is secured in container opening 536. Retention member 510 may be constructed of a polymeric material, such as an olefin, and other suitable materials. In embodiments of the wick assembly in which wick 310 is secured in retention member 510 with an interference fit, seals are formed between both wick 310 and retention member 510, and retention member 510 and container 20 to prevent leakage of the volatile liquid from container 20.

Forces acting on wick 310 (e.g., during handling of the wick by a user) may be sufficient to cause breakage of the wick. For example, referring to FIG. 3, if the portion of wick 310 residing outside container 20 is subjected to a force acting in a direction indicated by arrow "A" while the portion of wick 310 residing inside container 20 is prevented from moving, the applied force may be sufficient to cause breakage of wick 310. In such a case, it is desirable that the portion of wick 310 residing inside container opening 536 remains secured in opening 536 after breakage of wick 310 in order to prevent leakage of volatile liquid from container 20 through opening 536. To ensure that a portion of wick 310 remains in opening 536 after wick breakage, it is desirable to ensure that wick 310 breaks at a predetermined point along the length of the wick before breakage of any other component of wick assembly 500, such as container 20 or retention member 510, to which wick 310 is secured. The embodiments of wick assembly 500 described below incorporate breakage features therein which facilitate breakage of wick 310 at a predetermined location on the wick when a force is applied to the wick.

In one embodiment, the breakage feature incorporated into wick assemblies described herein comprises a discontinuity formed in an exterior surface of the wick. Referring to FIGS. 4, 5, 5a, 6 and 6a, the discontinuity in wick 310 may be formed by a junction 516 between two adjacent wick segments 512 and 514 secured in abutting contact with each other. Segments 512 and 514 may be constructed of different materials.

Figure 5:
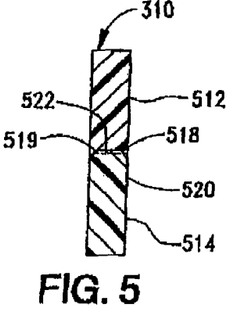
FIG. 5 is a cross-sectional view of an embodiment of the wick taken along line 5-5 in FIG. 4.
Figure 5A:
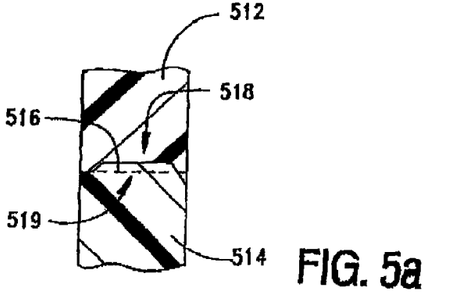
FIG. 5a is an enlarged partial view of the wick shown in FIG. 5.

Wick segments 512 and 514 may be secured in abutting contact using any of a variety of methods. In one embodiment, the method used for securing wick segments 512 and 514 together ensures a certain minimum, uninterrupted area of contact between wick segments 512 and 514 in order to provide sufficient migration of the volatile liquid from one wick segment to another. For example, as seen in FIGS. 5, 5a, 6 and 6a, segments 512 and 514 may be secured together using an adhesive substance applied at junction 516 between the segments. Referring to FIGS. 5 and 5a, in one example segment 512 has a depression 518 formed therein and segment 512 has an end portion 519 adapted to be received in depression 518. When end portion 519 is received in depression 518, segment 512 is engaged in abutting contact with segment 514 along a surface of segment 512 proximate depression 518. Segments 512 and 514 form a junction 516 on the surface of wick 310. In this embodiment, an adhesive material may be applied along either depression 518 or end portion 519 to bond end portion 519 to depression 518, thereby securing segment 512 in abutting contact with segment 514. In the event an adhesive is used to secure segments 512 and 514 together, an adhesive is preferably applied intermittently along the respective surfaces to keep open a capillary flow of volatile liquid upwardly through wick 310. Also, the adhesive to be applied is preferably of lesser resistance to sheer force than the wick 310 material itself.

Figure 6:
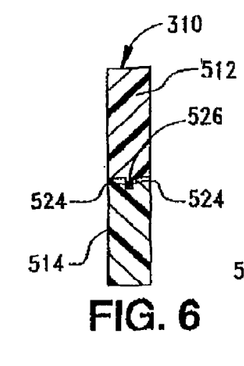
FIG. 6 is a cross-sectional view of a second embodiment of the wick shown in FIG. 4.
Figure 6A:
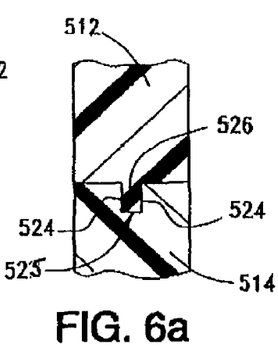
FIG. 6a is an enlarged partial view cross-sectional view of a central portion of the wick shown in FIG. 6.

Referring to FIGS. 6 and 6a, a second embodiment includes a depression 525 in segment 514 that has a pair of opposed walls 524. In this embodiment, an end portion of segment 512 includes a tab 526 adapted to be received between opposed walls 524 to form an interference fit therewith, thereby securing segment 512 in abutting contact with segment 514 along their mutual surfaces. Alternatively (or additionally), an adhesive may be applied to opposed walls 524 and/or to tab 526 to aid in securing segments 512 and 514 in abutting contact with each other. Again, the interference fit with or without adhesive should not be as resistant to sheer force as the wick 310 material itself.

Figure 7:
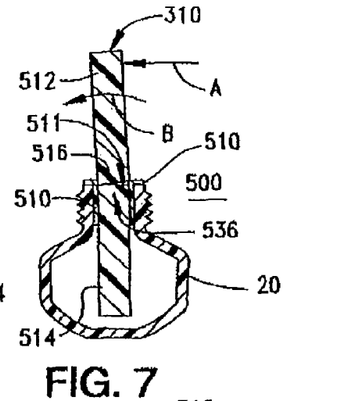
FIG. 7 is showing breakage of the wick in FIG. 5 under application of a force to the wick.

FIG. 7 shows an embodiment 500 of the wick assembly of the present invention. In this embodiment, wick 310 of one of the wick embodiments shown in FIGS. 5 and 6 is secured in opening 511 formed in retention member 510. In this embodiment, retention member 510 is secured in an opening 536 defined by container 20. Alternatively, wick 310a may be secured directly in opening 536 of container 20.

For reasons to be explained later, the wick 310 will generally be secured in either retention member 510 or container 20 such that a breakage feature incorporated into the wick resides proximate an end portion of retention member 510 or an end portion of container 20. For example, FIG. 7 shows an embodiment in which wick 310 is positioned in retention member opening 511 such that wick junction 516 resides proximate an end of retention member 510. If wick 310 were to be secured directly in container opening 536, wick 310 would be positioned in container opening 536 such that wick junction 516 would reside proximate an end of container opening 536.

Wick 310 may be secured in retention member opening 511 using an interference fit, adhesive, or other known methods. Any method used to secure wick 310 in retention member opening 511 should aid in preventing leakage of the volatile liquid along a path extending between wick 310 and retention member 510.

Similarly, retention member 510 may be secured in container opening 536 using an interference fit, adhesive, or other known methods. Any method used to secure retention member 510 within container opening 536 preferably aids in preventing leakage of the volatile liquid along a path extending between retention member 510 and container 20.

FIG. 7 shows the manner in which the breakage features of the present invention operate. The mode of operation shown applies generally to all embodiments of wick 310 and wick assembly 500 described herein.

Referring to FIG. 7, when a force is applied to wick 310 (for example, in the direction indicated by arrow "A") of wick assembly 500, tensile and compressive stresses are generated in the wick material. Application of a force to wick 310 incorporating one of the breakage features described herein may induce stresses in the wick material near the breakage feature which are greater than the stresses acting on adjacent, relatively homogeneous portions of wick 310. Additionally, the structure of wick 310 in the region of the breakage feature may be less resistant to stresses generated by application of the force due to inclusion of the breakage feature. Thus, formation of a breakage feature in a pre-determined region of wick 310 provides some predictability as to the location of a breaking point of wick 310 when a force is applied to the wick.

As seen in FIG. 7, when one portion 514 of wick is secured within container 20 while a force is applied in the direction of arrow "A" to another portion 512 of wick 310, retention member 510 acts as a pivot about which wick segment 512 may turn in a direction indicated by arrow "B". Application of sufficient force causes wick segment 512 to disengage from abutting contact with wick segment 514, pivot about retention member 510 and dislodge from retention member opening 511. If a retention member 510 is not employed, container 20 acts as a pivot and wick portion 512 breaks away from container 20 at container 20 opening.

Figure 8:
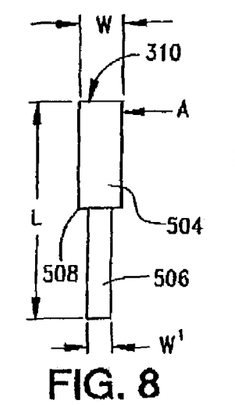
FIG. 8 is a side elevational view of a third embodiment of the wick.

Referring to FIG. 8, in a third embodiment of the wick 310, the discontinuity is formed by a junction 508 between a portion 504 of wick 310 and another, adjacent portion 506 of wick 310 having a different cross sectional area than portion 504. Wick 310 has one or more thickness dimensions W measured in a direction generally transverse to a length dimension L of wick 310. Generally, each thickness dimension will be smaller than length L. As seen in FIG. 8, wick 310 has multiple thickness dimensions W, W'. In a particular version of this embodiment, wick 310 has a cylindrical shape and portion 506 of wick 310 has a diameter different from portion 504 of wick 310.

Figure 9:
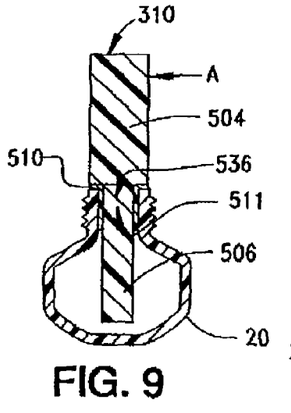
FIG. 9 is a cross-sectional view of an embodiment of the wick assembly showing the wick of FIG. 8 in a container for holding a volatile liquid to which it is secured.
Figure 10:
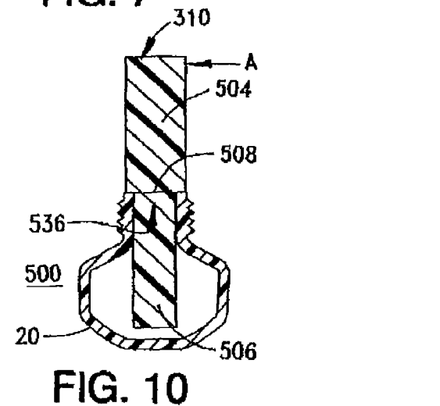
FIG. 10 is a cross-sectional view of the third embodiment of the wick of FIG. 9 in which the wick is fitted inside a retention member.

FIGS. 9 and 10 show the implementation of the third embodiment of wick. In wick assembly 500 (FIG. 9), wick 310 of FIG. 9 is secured in retention member 510, generally an annular plug discussed in more detail below, mounted in container opening 536 of container 20. In wick assembly 500 (FIG. 10), wick 310 is secured directly in container opening 536. Also, a portion 504 of wick 310 residing on a first side of the discontinuity will generally be positioned outside container 20, while another portion of wick 506 residing on an opposite side of the discontinuity will be positioned inside container 20. In this manner, as described above, positioning of the discontinuity or junction 508 in relation to container 20 in this example near the entrance of the opening 536 of container 20, provides predictability as to the location of a breaking point of wick 310 with respect to container 20 when force "A" is applied to wick 310. In this configuration any volatile liquid contained in container 20 will be blocked from spilling out of container 20 upon wick 310 breaking at junction 508.

Referring to FIGS. 9 and 10, when portion 506 of wick is secured within container 20 while a force in a direction indicated by arrow "A" is applied to portion 504 of wick 310, a region of relatively high stresses will be created at junction 508 between adjacent wick portions 504 and 506, due to the relatively abrupt change in cross-sectional area between the adjacent portions. If a sufficient force is applied to wick portion 504, retention member (or container 20) will act as a pivot, about which portion 504 may rotate. Thus, wick 310 will tend to break in the region of junction 508 rather than elsewhere along the length of wick 310.

Figure 11:
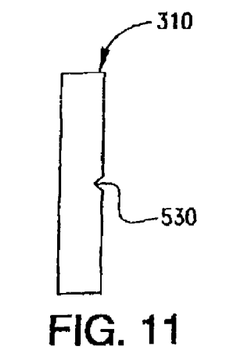
FIG. 11 is a side elevational view of a fourth embodiment of the wick of the present invention.

Referring to FIG. 11, in a fourth embodiment 310 of the wick, the discontinuity is in the form of a notch 530 formed in an exterior surface of wick 310. Notch 530 creates a region of stress concentration in the body of wick 310 during application of a force to wick 310. Thus, the stresses acting on the wick material in the region of this discontinuity due to an applied force will be greater than the stresses acting on adjacent, relatively homogeneous portions of the wick. Consequently, wick 310 will tend to break in the region of notch 530 rather than elsewhere along the length of the wick.

Figure 12:
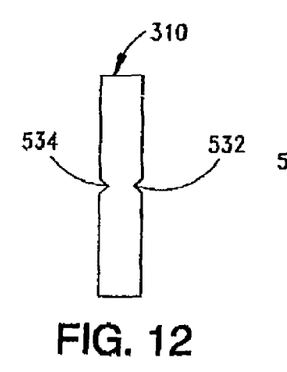
FIG. 12 is a side elevational view of a fifth embodiment of the wick of the present invention.

Referring to FIG. 12, in a fifth embodiment of the wick 310, multiple discrete notches 532 and 534 may be formed in the exterior surface of the wick. Although more notches may be formed in wick 310, only two notches are shown in FIG. 12 for purposes of clarity. In a sixth embodiment of the wick 310, shown in FIG. 13, a continuous notch 535 may be formed extending about a circumference of the body of wick 310.

Figure 13:
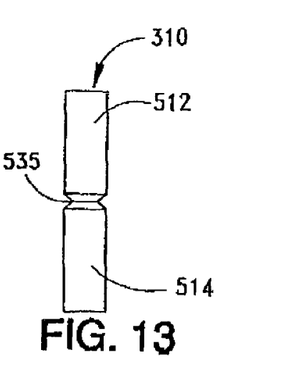
FIG. 13 is a side view of a sixth embodiment of the wick of the present invention.
Figures 14, 15, 17, 18, 19A, 19B, 20:
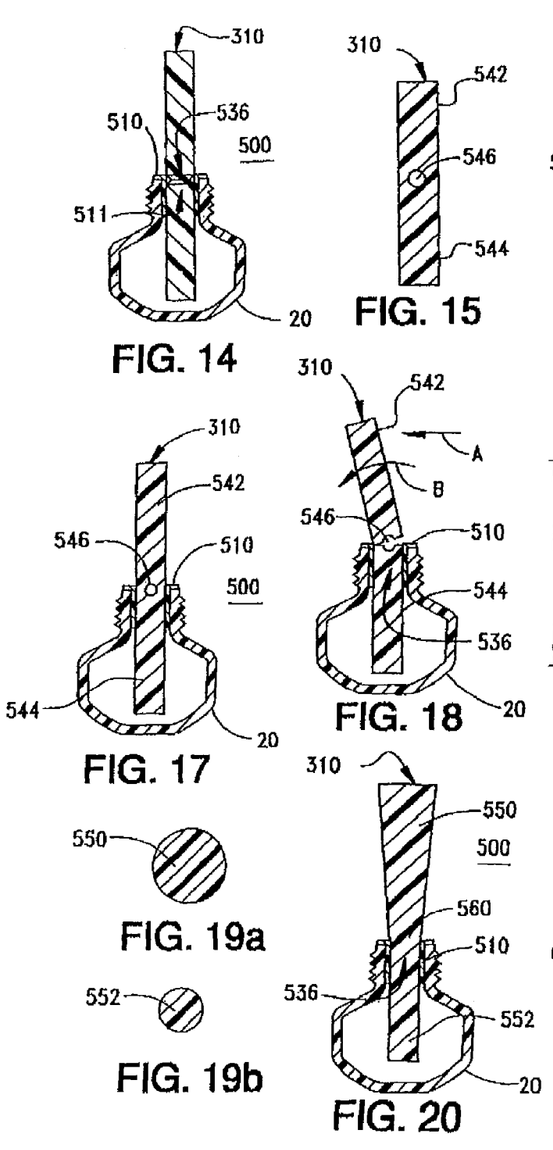
FIG. 14 is a cross-sectional view of the wick of FIG. 13 secured in a retention member mounted in a container for holding a volatile liquid.
FIG. 15 is a cross-sectional view of a seventh embodiment of the wick taken along the length of the wick.
FIG. 17 is a view of the embodiment of the wick shown in FIG. 15 secured in a retention member mounted in a container for holding a volatile liquid.
FIG. 18 is the wick assembly shown in FIG. 17 showing breakage of the wick in a predetermined location.
FIG. 19a is an enlarged cross-sectional view taken along line 19a-19a of FIG. 19.
FIG. 19b is an enlarged cross-sectional view taken along line 19b-19b of FIG. 19.
FIG. 20 is an enlarged cross-sectional view of a ninth embodiment of the wick of FIG. 19 secured in a retention member mounted in a container for holding a volatile liquid.

FIG. 14 shows employment of FIG. 13 wick 310 mounted in retention member 510 which is secured, in turn, in container opening 536 as described above. Wick 310 may alternatively be secured directly in container opening 511. Referring to FIG. 14, wick 310 is secured in retention member opening 511 such that notch 535 resides proximate an end of either retention member 510 or container opening 536 to provide a predictable pivot and breakage location along the wick, as described above.

Figure 16:
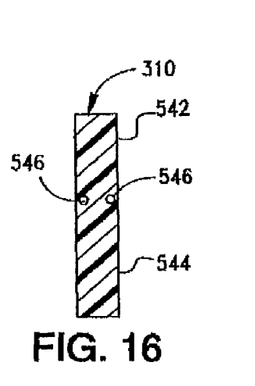
FIG. 16 is a cross-sectional view of an eighth embodiment of the wick taken along the length of the wick.

In another embodiment, the breakage feature incorporated into wick assemblies described herein comprises an absence of material formed in an interior portion of the wick. Referring to FIGS. 15 and 16 of the seventh and eighth embodiments, respectively, wicks 310 have elongated bodies and opposite ends 542 and 544. As stated above, wicks 310 may be formed from a plastic material such as nylon or high density polyethylene or the like and be substantially rigid.

In these embodiments, one or more absences 546 of the wick material are selectively positioned within the wick body intermediate ends 542 and 544. When the wick is formed from a plastic material, for example, absence (or absences) 546 may be formed by a blow molding process. In this process, a blow pin is inserted into a molten wick secured in a mold. Compressed air is then injected into the interior of the wick to displace a portion of the plastic in the wick interior.

Absence 546 creates a portion of the wick having a cross-sectional area less than adjacent portions of the wick which are substantially filled with the material from which the wick is formed. The pressure acting on the wick material along this reduced cross-sectional area due to an applied force will be greater than the pressure acting on adjacent, relatively homogeneous portions of the wick. Consequently, this reduced cross-sectional area provides less resistance to breakage than adjacent portions of the wick. In this manner, the forming of absence 546 in a pre-determined region of the wick provides some predictability as to the location of a breaking point of the wick when a force is applied to the wick.

FIG. 18 shows employment of the embodiment of wick 310 shown in FIG. 15. Wick 310 is secured in a retention member 510. Wick 310 may alternatively be secured directly in an opening 536 of a container 20 for holding the volatile liquid. As seen in FIG. 18, wick segment 542 resides outside container 20 while wick segment 544 is secured within container 20. In general, wick 310 is positioned with respect to an end portion of retention member 510 or container 20 such that an exterior surface of wick 310 that is proximate interior absence 546 resides proximate the end portion of retention member 510 or container 20.

As seen in FIG. 18, when a sufficient force is applied to the exposed end 542 of wick 310 in the direction indicated by arrow "A", retention member 510 acts as a pivot about which wick segment 542 will tend to rotate, in a direction indicated by arrow "B". Thus, when a sufficient force is applied to wick 310, the wick will tend to break proximate retention member 510, in the manner described previously.

Referring to FIGS. 19, 19a, 19b and 20, a ninth embodiment of the wick 310 comprises two segments 550 and 552 and a length L along which successive adjacent cross sectional areas of wick 310 taken generally transverse to length L vary along the length of the wick. As seen in the embodiments described above, wick 310 may be secured in either a retention member 510 or in a container 20. When wick 310 is secured in a retention member 510 or container 20, the variation in cross-sectional area of wick 310 generally occurs between segment 550 of wick 310 residing outside container 20, and a portion 560 residing proximate an end portion of either retention member 510 or container 20.

Referring to an example of this embodiment of wick 310 successive adjacent cross sectional areas of wick 310 vary uniformly along the length L of wick 310 between segment 550 of wick 310 and position 560 on the wick. In this embodiment, the areas of successive cross sections of wick 310 taken transverse to the wick will vary at a uniform rate, generally depending on the convergence or divergence of opposing exterior surfaces of the wick. In a particular embodiment, perimeters of successive adjacent cross sections of the wick taken generally transverse to the length will have substantially the same shape. For example, perimeters of successive adjacent cross sections taken along lines 19a-19a and 19b-19b (FIG. 19) will have substantially similar shapes, as shown in FIGS. 19a and 19b.

Referring to FIG. 20, wick 310 may have a pre-determined location 560 along its length at which a cross sectional area of the wick taken generally transverse to the length is less than or equal to a cross sectional area of wick 310 taken generally transverse to length L of wick 310 at any other location along the length of the wick. This location defines a cross section 560 having smallest area of any cross section taken transverse to length L of wick 310 in comparison to the wick portion 550 positioned outside of container 20. Due to the relatively small amount of wick material resisting a force applied to wick 310, the wick will tend to break at location 560 having the smallest cross sectional area, of the portion of the wick 550 outside of container 20, when a force is applied to wick segment 550.

As seen in FIG. 20, when wick 310 is secured in either retention member 510 or container 20 as described above, location 560 on wick 310 may be positioned proximate an end portion of either retention member 510 or container 20 to provide a predictable pivot and breakage location along length L of wick 310.

In the above-described embodiments, the wick is longitudinal, has a longitudinal axis and a curved exterior surface. In alternative embodiments, the wick may be formed such that a cross-section of the wick taken perpendicular to the longitudinal axis has any one of or a combination of a variety of simple geometric shapes, such as a circle, a diamond, a rectangle, a hexagon, an octagon, an oval or a triangle.

INDUSTRIAL APPLICABILITY

The present invention provides various features incorporated into a wick assembly that facilitate the breakage of a porous wick at a predetermined location on the wick when a force is applied to the wick. Generally, the wick is secured within an opening of a container for holding a volatile liquid, with a portion of the wick residing inside the container and a portion of the wick residing outside the container. The features described herein facilitate breakage of the wick before breakage of any other portion of the wick assembly (for example, the container). These features also help ensure that the portion of the wick secured in the container opening remains secured in the opening after wick breakage, thereby preventing leakage of the volatile liquid through the container opening.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved. All patents and patent applications referenced herein are incorporated by reference in the entireties thereof.

We claim:

1. A container for holding a volatile liquid and for use with a dispenser housing, the container comprising:
   a reservoir for holding the volatile liquid;
   an opening disposed in the reservoir; and a single structure molded porous wick disposed within the opening and having a first segment disposed within the reservoir and partially in contact with the volatile liquid and a second segment extending from the first segment and being fully outside the reservoir;

wherein the second segment of the wick includes successive adjacent cross sectional areas taken transverse to a length thereof that vary along the length thereof and wherein the successive cross sectional areas begin increasing at a point where a top edge of the container intersects the wick and increase in cross sectional area as the second segment moves away from the reservoir;

wherein the varying successive cross sectional areas provide an increasing surface area from which the volatile liquid may be emitted.

2. The container of claim 1, wherein the variation in cross sectional area of the second segment of the wick occurs at a uniform rate.

3. The container of claim 2, wherein the first segment of the wick has a generally uniform cross sectional area along a length thereof.

4. The container of claim 1, wherein perimeters of successive cross sectional areas have substantially the same shape.

5. The container of claim 4, wherein perimeters of successive cross sectional areas are all generally circular.

6. The container of claim 1, further including a retention member disposed in the opening for retaining the wick within the container.

7. The container of claim 1, wherein the cross sectional variation of the second segment begins at a point adjacent the opening of the container.

8. A container for holding a volatile liquid and for use with a dispenser housing, the container comprising:
a reservoir for holding the volatile liquid;
an opening disposed in the reservoir;
a retention member disposed within the opening; and
a wick retained within the opening by the retention member and having a first segment disposed within the reservoir and partially in contact with the volatile liquid and a second segment extending from the first segment and being fully outside the reservoir;

wherein the first segment of the wick disposed within the reservoir has a cross sectional area that is generally uniform along a length thereof and the second segment of the wick disposed outside the reservoir has successive adjacent cross sectional areas taken transverse to a length thereof that vary along the length thereof and wherein the successive cross sectional areas begin increasing at a point where a top edge of the retention member intersects the wick and continue increasing as the second segment moves away from the reservoir and, as the successive cross-sectional areas increase, a porosity of the wick is constant wherein the varying successive cross sectional areas provide an increasing surface area from which the volatile liquid may be emitted.

9. The container of claim 8, wherein the variation in cross sectional area of the second segment of the wick occurs at a uniform rate.

10. The container of claim 8, wherein perimeters of successive cross sectional areas have substantially the same shape.

11. The container of claim 10, wherein perimeters of successive cross sectional areas are all generally circular.

12. The container of claim 8, wherein the cross sectional variation of the second segment begins at a point adjacent the opening of the container.

13. A container for holding a volatile liquid and for use with a dispenser housing, the container comprising:
a reservoir for holding the volatile liquid;
an opening disposed in the reservoir;
a retention member disposed within the opening; and
a single structure molded porous wick disposed within the opening and having a first segment disposed within the reservoir and partially in contact with the volatile liquid and a second segment extending from the first segment and being fully outside the reservoir;

wherein, when the container is disposed within a volatile material dispenser, the second segment of the wick includes successive adjacent cross sectional areas taken transverse to a length thereof that vary along the length thereof and wherein the successive cross sectional areas increase in area beginning at a point where a top edge of the retention member intersects the wick and increase as the second segment moves away from the reservoir and, as the successive cross-sectional areas vary, a density of the wick is constant.

14. The container of claim 13, wherein the variation in cross sectional area of the second segment of the wick occurs at a uniform rate.

15. The container of claim 14, wherein the first segment of the wick has a generally uniform cross sectional area along a length thereof.

16. The container of claim 13, wherein perimeters of successive cross sectional areas have substantially the same shape.

17. The container of claim 16, wherein perimeters of successive cross sectional areas are all generally circular.

18. The container of claim 13, wherein the cross sectional variation of the second segment begins at a point adjacent the opening of the container.

* * * * *